United States Patent [19]

Okuda et al.

[11] Patent Number: 5,168,917
[45] Date of Patent: Dec. 8, 1992

[54] CASTING OF DENTAL METALS

[75] Inventors: Reiichi Okuda, Sendai; Norio Kojima, Ichikawa; Kenichi Iiyama, Tokyo; Yoshinobu Yamamura, Kawasaki; Yasutaro Ito; Shohei Hayashi, both of Tokyo, all of Japan

[73] Assignee: GC Corporation, Tokyo, Japan

[21] Appl. No.: 697,578

[22] Filed: May 9, 1991

[30] Foreign Application Priority Data

May 18, 1990 [JP] Japan ................................ 2-126964

[51] Int. Cl.⁵ .............................................. B22D 27/02
[52] U.S. Cl. ..................................... 164/495; 164/514
[58] Field of Search ................ 164/494, 495, 512, 514

[56] References Cited

U.S. PATENT DOCUMENTS 3,977,462  8/1976  Ohara .
4,254,817  3/1981  Kidowaki et al. ................... 164/514

FOREIGN PATENT DOCUMENTS 0018450  11/1980  European Pat. Off. .
63-273563  11/1988  Japan ................................. 164/495

Primary Examiner—Kuang Y. Lin
Attorney, Agent, or Firm—Oblon, Spivak, McClelland, Maier & Neustadt

[57] ABSTRACT

A method for casting dental metals with a casting apparatus including a melting chamber in which there are located an arc electrode above and a crucible formed of an electrically conductive material positioned below the arc electrode, and a mold chamber divided from the melting chamber by a partition wall having a through-hole at a position below the crucible and housing a mold box receiving a mold provided with an extending open vent positioned below the through-hole, the melting chamber communicating hermetically with the mold chamber through the mold, which is characterized by positioning a dental metal ingot on the crucible, vacuumizing the melting and mold chambers, feeding a small amount of an inert gas into the melting chamber at such a pressure as to induce arc discharge all over the upper surface of the ingot, thereby melting the ingot placed on the crucible by arc discharge from the arc electrode, pouring the thus obtained molten metal into the mold through its inlet, and immediately feeding an additional amount of the inert gas into the melting chamber to increase its internal pressure to a level suitable for casting.

2 Claims, 3 Drawing Sheets

CASTING OF DENTAL METALS

BACKGROUND OF THE INVENTION

1. Field of the Invention

The present invention relates to a method for casting such dental metals as titanium designed to make plate frames, clasps, etc. in the dental technical field, which enables high-quality products to be cast with neither casting deficiencies nor casting cavities by melting dental metal ingots by arc discharge.

2. Statement of the Prior Art

In the dental technical field, titanium has been used for CAST PLATES, clasps, etc., because it is light in weight, has a certain or more strength and excels in corrosion resistance and bioaffinity.

So far, metal frames, etc. used for, e.g. crowns or porcelain-fused-to-metal crowns have been cast by melting dental metals in the atmosphere with the use of suitable techniques such as high-frequency melting and pouring the molten metals in molds, because the dental metals are noble metal alloys relatively difficult to oxidize. Since the above-mentioned titanium has the property of being likely to undergo oxidization, however, it should be melted in an atmosphere of such an inert gas as argon. To meet such demand, reliance has been placed on a casting technique wherein dental metal ingots are melted by arc discharge and the obtained molten metals are poured in molds.

According to this casting technique, an arc electrode is disposed above in a hermetically sealed melting chamber, and a crucible made of an electrically conductive material is positioned just below the arc electrode. With the arc electrode and crucible connected to a cathode and an anode, respectively, the dental metal ingot to be cast is first placed on the crucible. After evacuation to vacuum, the melting chamber is then filled with such an inert gas as argon until its internal pressure amounts to a pressure nearly equal to atmospheric pressure. Subsequently, the ingot is melted by arcs occurring from the arc electrode. Finally, the molten metal is poured in a mold chamber through the inlet of a mold located in it, said mold chamber being partitioned from said melting chamber by a partition wall provided with a through-hole formed in its portion positioned below said crucible.

When titanium is used with this casting technique, it should be rapidly poured into the mold through its inlet, partly because its melting point is higher than those of common dental metals, and partly because it has to be cast with the mold maintained at room temperature, so that it cools down and solidify rapidly—due to the fact that it reacts with mold material at such a high temperature as in casting common noble metal alloys. In other words, titanium must be poured under pressure into the mold by increasing pressure in the melting chamber to make a pressure difference between the melting chamber and the mold chamber.

The mold used is constructed from investment material composed of a binder/aggregate combination. More specifically, the binder and aggregate are kneaded together with water or an exclusive liquid into slurry. After that, a wax model is invested in the slurry, followed by burning out wax at about 700° C. in furnace.

Owing to having some air permeability, such investment material may be used for casting noble metal alloys forming part of metal frames, etc. used for crowns or porcelain-fused-to-metal crowns. This is because if it is pressurized with a pressure difference made between the melting and mold chambers, then an increase in the in-mold gas pressure is so suppressed by its air permeability that the molten dental metal can be well poured into the mold.

Among common investment materials, however, there is a gypsum-bonded investment material using gypsum as the binder. At 700° C. or higher, this material increases in air permeability and decreases in heat resistance, since gypsum decomposes thermally at that temperature and so cannot retain its crystal form. For instance, when a high temperature dental metal like titanium is cast with that investment material, they react with each other to evolve such amount of gases that the gases cannot escape only through the inherent air permeability the investment material inherently has. This would increase the pressure in the casting region of the mold, making it impossible to pour the predetermined amount of the molten dental metal in the mold. Otherwise gases would be entrained in the molten metal, giving rise to cavities. In order to cast a high temperature dental metal, use has thus been made of a phosphate-bonded investment material using a phosphate as the binder. With this phosphate type of a material in which the binder phosphate combines with a metal oxide to form an amorphous product, gas emissions are limited even upon heated at high temperatures, since it undergoes no or little change in state and is of increased heat resistance. However, this leads to another defect that its air permeability is badly limited. For that reason, it has been proposed to use coarse aggregates for increased air permeability, thereby reducing a pressure rise in the casting regions of molds when the molten dental metal are poured in the casting regions. However, this method makes the surfaces of casting products rough, nonetheless, fails to obtain sufficient air permeability.

Thus, when no sufficient air permeability is obtained, the internal pressure in the casting region of the mold is increased too much to pour the predetermined amount of the molten dental metal into the mold. This gives rise to such disadvantages as casting deficiencies and entrainment of gases in the molten metal, resulting in casting cavities.

Arc melting of a dental metal ingot at around atmospheric pressure causes arcs to concentrate on its local points under the influences of magnetic blow, etc., often making its uniform melting impossible and thereby causing it to be locally heated to high temperatures. When the dental metal ingot melts in its entirety, the molten dental metal reacts with the crucible material. In order to prevent this, additional special mechanisms for moving the electrodes are needed.

In order to obviate the above-mentioned defects of the prior art, the present invention seeks to provide a method for casting dental metals, which can give well-smoothened castings by stable arc melting with no fear of causing casting deficiencies or cavities.

SUMMARY OF THE INVENTION

We have made strenuous studies to achieve the above-mentioned object and so have invented a method for casting dental metals with a casting apparatus including a melting chamber in which there are located an arc electrode above and a crucible formed of an electrically conductive material positioned below said arc electrode, and a mold chamber divided from said melting chamber by a partition wall having a through-hole at a position below said crucible and housing a mold box receiving a mold provided with an extending open vent positioned below said through-hole, said melting chamber communicating hermetically with said mold chamber through said mold, said method being characterized by positioning a dental metal ingot on said crucible, vacuumizing said melting and mold chambers, feeding a small amount of an inert gas into said melting chamber at such a pressure as to induce arc discharge all over the upper surface of said ingot, thereby melting said ingot placed on said crucible by arc discharge from said arc electrode, pouring the thus obtained molten metal into said mold through its inlet, and immediately feeding an additional amount of the inert gas into the said melting chamber to increase its internal pressure to a level suitable for casting.

According to this invention, uniform arc melting of dental metal ingots is achievable, since local arc discharge can be prevented by keeping low the pressure of the internal gas in the melting chamber in which they are positioned.

According to this invention, the defect of casting deficiencies and cavities are caused by a fact that the inner pressure of the mold increased when the molten dental metal is poured into the inlet of the mold, since it is difficult to impart sufficient air permeability to the investment material. Such defect- or cavity-free castings can be obtained by keeping the internal pressure of the melting and mold chambers low until dental metal ingots are melted and poured into a mold through its inlet, and feeding an additional amount of the inert gas into the melting chamber immediately following the pouring of the molten metal into the mold through its inlet.

According to a preferable embodiment of this invention wherein the additional amount of the inert gas is rapidly supplied into the melting chamber through a gas tank positioned in the vicinity of the melting chamber, it is possible to obtain castings of even higher quality. This is never achieved with common inert gas cylinders which cannot supply large volumes at a time.

BRIEF DESCRIPTION OF THE DRAWINGS

The present invention will now be explained, by way of example alone, with reference to the accompanying drawings in which.

DETAILED EXPLANATION OF THE INVENTION

Figure 1:
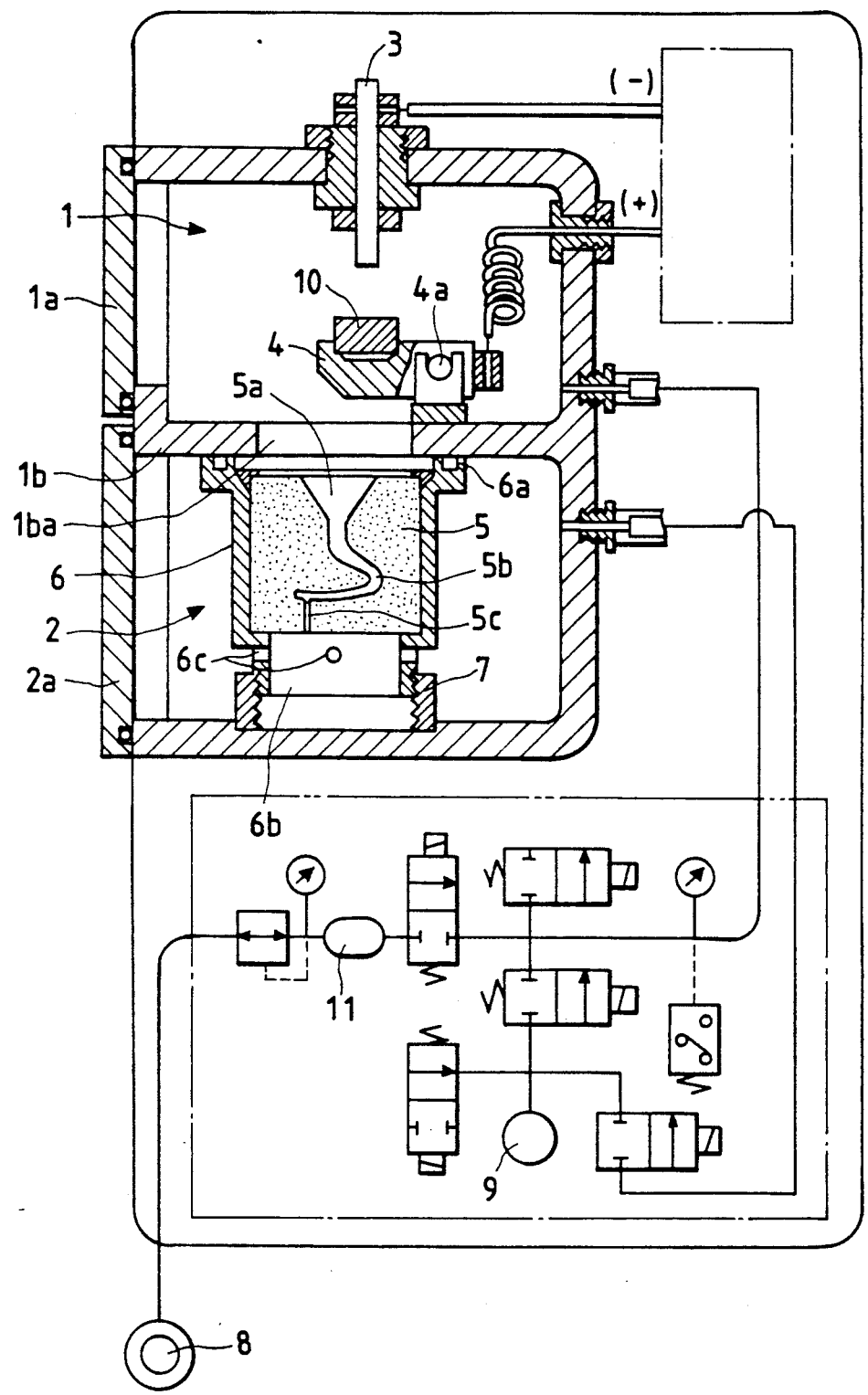
FIG. 1 is a view illustrating an important part of one embodiment of the casting apparatus for carrying out this invention.

In order to carry out the method of this invention, there is first provided a hermetically maintained casting system divided by a partition wall $1b$ having a through-hole $1ba$ into melting chamber 1 and mold chamber 2, as illustrated in FIG. 1. The melting chamber 1, preferably together with the mold chamber 2, is evacuated to substantial vacuum by means of a vacuum pump 9, and is designed to be provided with an inert gas such as argon through an inert gas supply source 8. In the vicinity of the melting chamber 1 and someplace on a pipe for making communication between the gas source 8 and the melting chamber 1, there is preferably located a tank 11, which is adapted to receive the inert gas from the gas source 8 and feed it into the melting chamber 1 rapidly. This pipe includes an electromagnetic valve for regulating the amount of the inert gas fed. In the melting chamber 1, there are an arc electrode 3 located above and a crucible 4 formed of an electrically conductive material, which is located just below the arc electrode 3, said arc electrode 3 and said crucible 4 being connected to a cathode and an anode, respectively. Preferably, the crucible 4 used is designed to turn up or down pivotally around a horizontal shaft $4a$ as shown in FIG. 1. However, other preferable types of crucibles, for instance, is one having an openable opening in the bottom (not shown), may be used. In this arrangement, the mold chamber 2 is positioned just below the through-hole $1ba$ formed through the partition wall $1b$ located below the crucible 4, and includes therein a cylindrical mold box 6, which is open at its lower end, as shown in FIG. 1. Then, a mold 5 including an open vent $5a$ extending through it is housed in this mold box 6 with its lower zone $6b$ in threaded engagement with a seal setter 7 and its upper zone $6a$ abutting against the lower side of said partition wall $1b$, i.e. being horizontally sealed. In order to seal this mold box 6, a V-shaped packing (not shown) may be provided around its upper zone $6a$ such that it abuts against the vertical plane of the through-hole $1ba$ in the partition wall $1b$. As illustrated in FIG. 1, a communication hole $6c$ is formed through the lower zone $6b$ of the mold box 6 or the seal setter 7 (through the former in this embodiment). Thus, the mold chamber 2 communicates with the melting chamber 1 through the open vent $5a$ having a very small diameter, which may be said to be a "communication channel" for making communication between the casting region $5b$ of the mold 5 and its outside.

Figure 2:
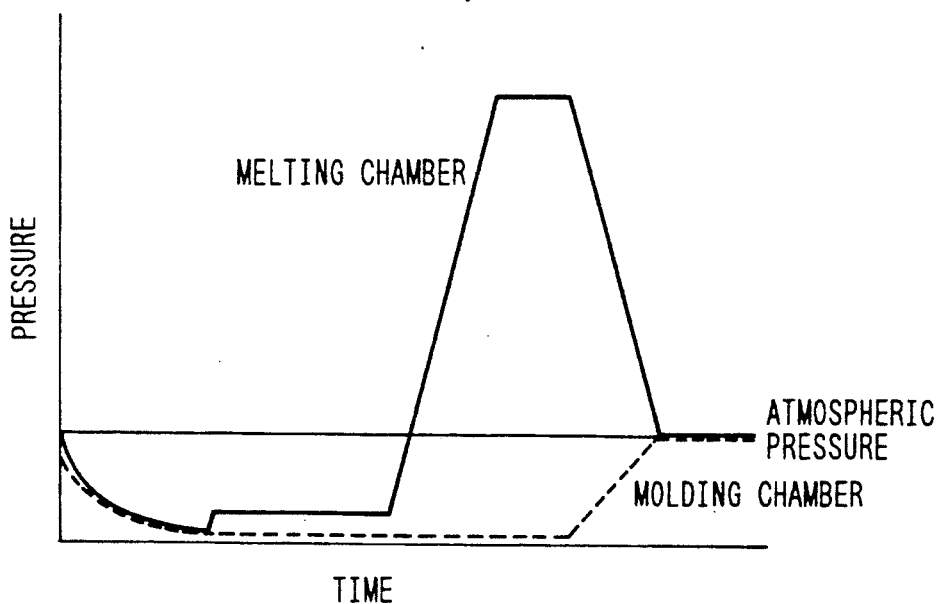
FIG. 2 is a graphical view showing pressure changes in the melting and mold chambers, when the method of this invention is carried out with the casting apparatus of FIG. 1.

Casting of dental metal products with the casting apparatus may be carried out while controlling the internal pressures of the melting and mold chambers 1 and 2 as shown in FIG. 2 by way of example.

First, the mold box 6 with the mold 5 housed in it is positioned in place within the mold chamber 2 while the seal setter 7 is in threaded engagement with its lower zone $6b$. Then, the mold box 6 or seal setter 7 is turned to force the mold box 6 to bring its upper zone $6a$ into sealing engagement with the partition wall $1b$, and the door $2a$ is closed to make the mold chamber 2 and melting chambers 1 hermetic. In this state, the mold chamber 2 communicates with the melting chamber 1 through the communication hole $6c$ formed through the lower zone $6b$ of the mold box 6 or the seal setter 7 and the open vent $5a$ extending through the mold 5.

Then, a dental metal ingot 10 is placed on the crucible 4 located in the melting chamber 1, followed by closure of the door $1a$ to make the melting chamber 1 hermetic.

In this state, the melting chamber 1 is evacuated to vacuum by means of the vacuum pump 9, so that the mold chamber 2 is substantially vacuumized. However, it is preferred that the mold chamber 2 is similarly evacuated by the vacuum pump 9 to vacuumize it substantially, since the open vent $5a$ defines the channel having a small diameter.

Figure 3A:
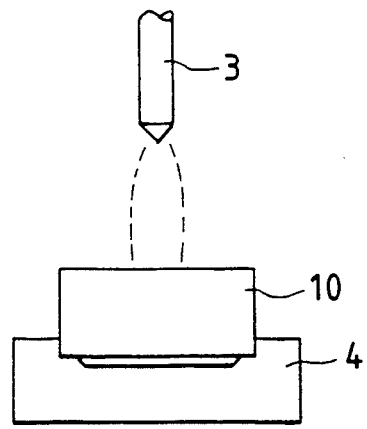
FIG. 3 is views showing what state of arcs when the pressure in the melting chamber is 3(A) substantially atmospheric pressure, 3(B) is in a preferred condition, and 3(C) is close to vacuum.
Figure 3B:
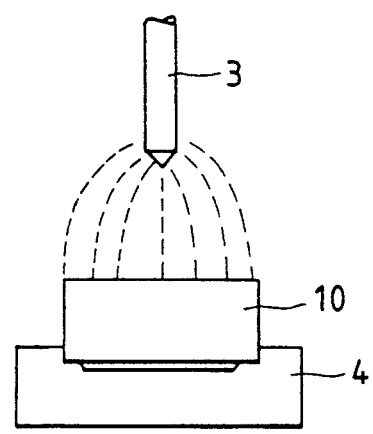
Figure 3C:
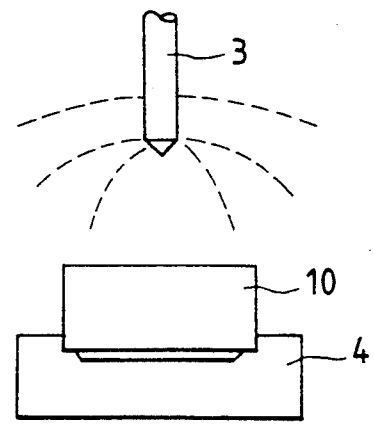

After that, a trace amount of an inert gas such as argon is suppoed from the gas source into the melting chamber 1 at such a pressure as to allow arc discharge to be generated all over the upper surface of the ingot 10. Subsequent arc discharge from the arc electrode 3 melts the ingot 10 placed on the crucible 4. In the instant embodiment, the arc electrode 3 used is constructed from tungsten and is 4 mm in diameter, and the ingot 10 made of titanium in a columnar form having a diameter 40 mm and a height of 12 mm is placed on the crucible 4. When the electrode 3 is spaced 7 mm away from the titanium ingot 10, arc discharge is induced all over the upper surface of the ingot 10 at an arc current of 250 A in an argon gas atmosphere of 5 to 150 Torr, as illustrated in FIG. 3(B). However, if the melting chamber 1 is fixed at a pressure nearly equal to atmospheric pressure, as illustrated in FIG. 3(A), then arcs become so fine that they concentrate on the ends of the ingot 10 under the influences of magnetic blow, etc., causing its local melting, and if the melting chamber 1 is kept at a pressure nearly equal to vacuum, as illustrated in FIG. 3(C), then arcs spread so excessively that the ingot 10 will not melt. According to this embodiment, it is possible to melt the dental metal ingot 10 within a short time yet with improved efficiency and establish a delicate pressure condition just before casting.

The thus molten dental metal is poured into the mold 5 through its inlet 5a. If the crucible 4 is designed to turn up or down pivotally around the horizontal shaft 4a, as illustrated in FIG. 1, it is then preferred to pour the molten metal into the mold 5 through its inlet 5a, while electrical current remains conducting between the electrode 3 and the crucible 4. This is because when the crucible 4 turns down, the arc electrode 3 is so spaced away from the molten metal, i.e., distance between the electrodes is so spaced away, that arc discharge can cease automatically. As a result, the molten metal can be heated until immediately before it will be poured into the mold 5 through its inlet 5a. When the crucible 4 used is designed to have an openable opening in its bottom, arc discharge is stopped after the melting of the metal ingot 10. Immediately after that, the opening is held open to pour the molten metal into the mold 5 through its inlet 5a.

Just after the molten metal has been poured into the mold 5 through its inlet 5a, an additional amount of the inert gas, e.g. argon is supplied from the gas source 8 into the melting chamber 1 to increase its internal pressure, thereby applying pressure to the molten metal from the melting chamber 1. Thereupon, gases present in the mold 5, which is provided with the open vent 5c, are dissipated into the mold chamber 2 through that open vent 5c and the communication hole 6c in the mold box 6 or the seal setter 7. In this manner, it is possible to prevent the gases from being compressed within the mold 5 and increasing the internal pressure of the casting region 5b of the mold 5. In this case, while there is some increase in the pressure of the mold chamber 2 due to the gases in the mold 5, pressurization of the molten metal is well achieved, the pressurized state of the molten dental metal is not prevented since the gases entering the mold chamber 2 are very small relative to the volume of the melting chamber 1. At this time, the tank 11 having the same volume as that of the melting chamber 1, located in the vicinity of the melting chamber 1 assures sufficiently rapid pressure rises to occur in the melting chambe, enabling casting to be completed with high casting capabilities.

According to the casting method of this invention which has been explained in greater detail, dental metals can be cast by arc melting occurring at a pressure of an inert gas such as argon gas, so small that arcs spread uniformly all over the upper surfaces of dental metal ingots to melt them simultaneously in their entirety. Thus melting deficiencies due to local arc discharge or disadvantages such as the reaction of molten dental with crucibles are eliminated, while special means for moving electrodes, etc. are dispensed with. Dental metals are unlikely to undergo oxidation, since their casting processes from pouring into the mold to hardening occur in an inert gas atmosphere. Rapid and assured pouring of molten dental metal into molds is achieved, partly because the in-mold pressure is kept low when the molten dental metals are poured into the molds, and partly because as the molten dental metals are poured into the molds, gases therein are dissipated into the mold chambers through the open vents, so that the internal pressures of the molds are kept low, whereby when the molten dental metals are poured into the molds under pressure at an elevated in-melting chamber pressure, it is possible to maintain a pressurized melt downstream from the melting chambers toward the molds. As the molten dental metal are designed to pour into molds at a low in-mold pressure, gases are in a pressure condition so low that they cannot be entrained in the molten dental metal. If the additional amount of the inert gas is supplied into the melting chamber through a gas tank located in the vicinity thereof, then it is possible to increase the rate of casting, thereby obtaining defect- or cavity-free castings. Thus well-smoothened castings can be obtained using as the investment material a phosphate material having a limited air permeability.

As summarized above, the present method has various advantages of being able to produce dental metal products easily and securely by low-pressure melting and casting without causing casting deficiencies or casting cavities and so makes a great contribution to the dental processing field.

What we claim is:

1. A method for casting dental metals with a casting apparatus including a melting chamber in which there are located an arc electrode and a crucible formed of an electrically conductive material positioned below said arc electrode, and a mold chamber divided from said melting chamber by a partition wall having a through-hole at a position below said crucible and housing a mold box receiving a mold provided with an extending open vent positioned below said through-hole, said melting chamber communicating hermetically with said mold chamber through said mold, said method comprising the steps of:

positioning a dental metal ingot on said crucible,
 vacuumizing said melting and mold chambers,
 feeding a small amount of an inert gas into said melting chamber to produce a pressure of between 5 torr and 150 torr in said melting chamber to induce arc discharge all over the upper surface of said ingot, thereby melting said ingot placed on said crucible by arc discharge from said arc electrode,
 pouring the thus obtained molten metal into said mold through an inlet, and
 immediately feeding an additional amount of the inert gas into said melting chamber to increase its internal pressure to a level suitable for casting.

2. A method as claimed in claim 1, wherein said additional amount of the inert gas is rapidly fed into said melting chamber through a gas tank located in the vicinity of said melting chamber to increase internal pressure to a level suitable for casting immediately after pouring the thus obtained molten metal into said mold through the said inlet.

* * * * *